(12) United States Patent
McGill

(10) Patent No.: US 7,270,803 B1
(45) Date of Patent: Sep. 18, 2007

(54) HIGH-CLEANING, LOW ABRASION, HIGH BRIGHTNESS SILICA MATERIALS FOR DENTRIFICES

(75) Inventor: Patrick D. McGill, Darlington, MD (US)

(73) Assignee: J.M. Huber Corporation, Edison, NJ (US)

( * ) Notice: Subject to any disclaimer, the term of this patent is extended or adjusted under 35 U.S.C. 154(b) by 0 days.

(21) Appl. No.: 11/387,299

(22) Filed: Mar. 23, 2006

(51) Int. Cl.
*A61K 8/00* (2006.01)
*A61K 8/18* (2006.01)
*A61K 11/00* (2006.01)
*C00B 33/12* (2006.01)

(52) U.S. Cl. .......................... 424/49; 424/52; 424/54; 516/82; 516/113; 423/335; 423/339; 51/308

(58) Field of Classification Search .................. None
See application file for complete search history.

(56) References Cited

U.S. PATENT DOCUMENTS

| | | |
|---|---|---|
| 3,538,230 A | 11/1970 | Pader et al. |
| 3,577,521 A | 5/1971 | Scheller et al. |
| 3,967,563 A | 7/1976 | Wason |
| 3,988,162 A | 10/1976 | Wason |
| 4,122,161 A | 10/1978 | Wason |
| 4,153,680 A | 5/1979 | Seybert |
| 4,303,641 A | 12/1981 | DeWolf, II et al. |
| 4,420,312 A | 12/1983 | Wason |
| 4,618,488 A | 10/1986 | Maeyama et al. |
| 4,632,826 A | 12/1986 | Ploger et al. |
| 4,992,251 A | 2/1991 | Aldcroft et al. |
| 5,035,879 A | 7/1991 | Aldcroft et al. |
| 5,098,695 A | 3/1992 | Newton et al. |
| 5,124,143 A | 6/1992 | Muhlemann |
| 5,234,673 A | 8/1993 | McGill et al. |
| 5,419,888 A | 5/1995 | McGill et al. |
| 5,647,903 A | 7/1997 | McGill et al. |
| 5,651,958 A | 7/1997 | Rice |
| 5,658,553 A | 8/1997 | Rice |
| 5,869,028 A * | 2/1999 | McGill et al. ............. 424/49 |
| 5,891,421 A | 4/1999 | McGill et al. |
| 6,159,277 A * | 12/2000 | Tanaka et al. ............. 106/272 |
| 6,290,933 B1 | 9/2001 | Durga et al. |
| 6,740,311 B2 * | 5/2004 | White et al. ............. 424/49 |

FOREIGN PATENT DOCUMENTS

WO  03/055802 A1  7/2003

OTHER PUBLICATIONS

Barrett, Elliott P., et al., "The Determination of Pore Volume and Area Distributions in Porous Substances. I. Compoutations from Nitrogen Isotherms", *The Volume and Area Distributions in Porous Substances*, vol. 73, pp. 373-380, Jan. 1951, The British Library.
Wason, S. K., "Cosmetic properties and structure of fine-particle synthetic precipitated silicas", *J. Soc. Cosmet. Chem.*, 29, pp. 497-521 (Aug. 1978).

* cited by examiner

*Primary Examiner*—Frederick Krass
(74) *Attorney, Agent, or Firm*—Carlos Nieves; William Parks

(57) ABSTRACT

Unique abrasive materials that are in situ generated compositions of precipitated silicas and silica gels are provided. Such compositions exhibit different beneficial, particularly simultaneously high pellicle film cleaning properties and moderate dentin abrasion levels. Such a result thus accords the user a dentifrice that effectively cleans tooth surfaces without detrimentally abrading such surfaces. Furthermore, the produced abrasive materials also exhibit very high and desirable brightness properties that permit easy incorporation and utilization within dentifrices for aesthetic purposes. Encompassed within this invention is a unique method for making such gel/precipitated silica composite materials for such a purpose, particularly under high shear conditions, as well as the different materials within the structure ranges described above and dentifrices comprising such.

10 Claims, No Drawings

HIGH-CLEANING, LOW ABRASION, HIGH BRIGHTNESS SILICA MATERIALS FOR DENTRIFICES

FIELD OF THE INVENTION

This invention relates to unique abrasive materials that are in situ generated compositions of precipitated silicas and silica gels. Such compositions exhibit different beneficial, particularly simultaneously high pellicle film cleaning properties and moderate dentin abrasion levels. Such a result thus accords the user a dentifrice that effectively cleans tooth surfaces while controlling the amount of abrasion applied to the surfaces of the subject teeth. Furthermore, the produced abrasive materials also exhibit very high and desirable brightness properties that permit easy incorporation and utilization within dentifrices for aesthetic purposes. Encompassed within this invention is a unique method for making such gel/precipitated silica composite materials for such a purpose, particularly under high shear conditions, as well as the different materials within the structure ranges described above and dentifrices comprising such.

BACKGROUND OF THE PRIOR ART

An abrasive substance has been included in conventional dentifrice compositions in order to remove various deposits, including pellicle film, from the surface of teeth. Pellicle film is tightly adherent and often contains brown or yellow pigments which impart an unsightly appearance to the teeth. While cleaning is important, the abrasive should not be so aggressive so as to damage the teeth. Ideally, an effective dentifrice abrasive material maximizes pellicle film removal while causing minimal abrasion and damage to the hard tooth tissues. Consequently, among other things, the performance of the dentifrice is highly sensitive to the extent of abrasion caused by the abrasive ingredient. Conventionally, the abrasive cleaning material has been introduced in flowable dry powder form to dentifrice compositions, or via redispersions of flowable dry powder forms of the polishing agent prepared before or at the time of formulating the dentifrice. Also, and more recently, slurry forms of such abrasives have been provided to facilitate storage, transport, and introduction within target dentifrice formulations.

Synthetic low-structure silicas have been utilized for such a purpose due to the effectiveness such materials provide as abrasives, as well as low toxicity characteristics and compatibility with other dentifrice components, such as sodium fluoride, as one example. When preparing synthetic silicas, the objective is to obtain silicas which provide maximal cleaning with minimal impact to the hard tooth surfaces. Dental researchers are continually concerned with identifying abrasive materials that meet such objectives.

Synthetic silicas (of higher structure) have also been utilized as thickening agents for dentifrices and other like paste materials in order to supplement and modify the rheological properties for improved control, such as viscosity build, stand up, brush sag, and the like. For toothpaste formulations, for example, there is a need to provide a stable paste that can meet a number of consumer requirements, including, and without limitation, the ability to be transferred out of a container (such as a tube) via pressure (i.e., squeezing of the tube) as a dimensionally stable paste and to return to its previous state upon removal of such pressure, the ability to be transferred in such a manner to a brushhead easily and without flow out of the tube during and after such transference, the propensity to remain dimensionally stable on the brush prior to use and when applied to target teeth prior to brushing, and the exhibiting of proper mouthfeel for aesthetic purposes, at least, for the benefit of the user.

Generally, dentifrices comprise a majority of a humectant (such as sorbitol, glycerin, polyethylene glycol, and the like) in order to permit proper contact with target dental subjects, an abrasive (such as precipitated silica) for proper cleaning and abrading of the subject teeth, water, and other active components (such as fluoride-based compounds for anticaries benefits). The ability to impart proper rheological benefits to such a dentifrice is accorded through the proper selection and utilization of thickening agents (such as hydrated silicas, hydrocolloids, gums, and the like) to form a proper network of support to properly contain such important humectant, abrasive, and anticaries ingredients. It is thus evident that formulating proper dentifrice compositions can be rather complex, both from a compounding standpoint as well as the number, amount, and type of components present within such formulations. As a result, although it is not a high priority within the dentifrice industry, the ability to reduce the number of such components, or attempt to provide certain components that meet at least two of these needed properties could potentially reduce formulation complexity, not to mention potentially reducing the overall manufacturing costs.

A number of water-insoluble, abrasive polishing agents have been used or described for dentifrice compositions. These abrasive polishing agents include natural and synthetic abrasive particulate materials. The generally known synthetic abrasive polishing agents include amorphous precipitated silicas and silica gels and precipitated calcium carbonate (PCC). Other abrasive polishing agents for dentifrices have included chalk, magnesium carbonate, dicalcium phosphate and its dihydrate forms, calcium pyrophosphate, zirconium silicate, potassium metaphosphate, magnesium orthophosphate, tricalcium phosphate, perlite, and the like.

Synthetically-produced precipitated low-structure silicas, in particular, have been used as abrasive components in dentifrice formulations due to their cleaning ability, relative safeness, and compatibility with typical dentifrice ingredients, such as humectants, thickening agents, flavoring agents, anticaries agents, and so forth. As known, synthetic precipitated silicas generally are produced by the destabilization and precipitation of amorphous silica from soluble alkaline silicate by the addition of a mineral acid and/or acid gases under conditions in which primary particles initially formed tend to associate with each other to form a plurality of aggregates (i.e., discrete clusters of primary particles), but without agglomeration into a three-dimensional gel structure. The resulting precipitate is separated from the aqueous fraction of the reaction mixture by filtering, washing, and drying procedures, and then the dried product is mechanically comminuted in order to provide a suitable particle size and size distribution.

The silica drying procedures are conventionally accomplished using spray drying, nozzle drying (e.g., tower or fountain), wheel drying, flash drying, rotary wheel drying, oven/fluid bed drying, and the like.

As it is, such conventional abrasive materials suffer to a certain extent from limitations associated with maximizing cleaning and minimizing dentin abrasion. The ability to optimize such characteristics in the past has been limited generally to controlling the structures of the individual components utilized for such purposes. Examples of modifications in precipitated silica structures for such dentifrice purposes are described in the art within such publications as U.S. Pat. Nos. 3,967,563, 3,988,162, 4,420,312, and 4,122,161 to Wason, U.S. Pat. Nos. 4,992,251 and 5,035,879 to Aldcroft et al., U.S. Pat. No. 5,098,695 to Newton et al., and U.S. Pat. Nos. 5,891,421 and 5,419,888 to McGill et al. Modifications in silica gels have also been described within such publications as U.S. Pat. No. 5,647,903 to McGill et al., U.S. Pat. No. 4,303,641, to DeWolf, II et al., U.S. Pat. No. 4,153,680, to Seybert, and U.S. Pat. No. 3,538,230, to Pader et al. Such disclosures teach improvement in such silica materials in order to impart increased pellicle film cleaning capacity and reductions in dentin abrasion levels for dentifrice benefits. However, these typical improvements lack the ability to deliver preferred property levels that accord a dentifrice producer the ability incorporate such an individual material in different amounts with other like components in order to effectuate different resultant levels of such cleaning and abrasion characteristics. To compensate for such limitations, attempts have been undertaken to provide various combinations of silicas to permit targeting of different levels. Such silica combinations involving compositions of differing particle sizes and specific surface areas are disclosed in U.S. Pat. No. 3,577,521. to Karlheinz Scheller et al., U.S. Pat. No. 4,618,488 to Macyarea et al., U.S. Pat. No. 5,124,143 to Muhlemann, and U.S. Pat. No. 4,632,826 to Ploger et al. Such resultant dentifrices, however, fail to provide desired levels of abrasion and high pellicle cleaning simultaneously.

Another attempt has been made to provide physical mixtures of precipitated silicas of certain structures with silica gels, notably within U.S. Pat. No. 5,658,553 to Rice. It is generally accepted that silica gels exhibit edges, and thus theoretically exhibit the ability to abrade surfaces to a greater degree, than precipitated silicas, even low structured types. Thus, the blend of such materials together within this patent provided, at that time, an improvement in terms of controlled but higher levels of abrasiveness coupled with greater pellicle film cleaning ability than precipitated silicas alone. In such a disclosure, it is shown that separately produced and co-incorporated silica gels and precipitated silicas can permit increased PCR and RDA levels but with apparently greater control for lower abrasive characteristics than for previously provided silicas exhibiting very high PCR results. Unfortunately, although these results are certainly a step in the right direction, there is still a largely unfulfilled need to provide a silica-based dental abrasive that exhibits sufficiently high pellicle film cleaning properties with simultaneously lower radioactive dentin abrasive characteristics such that film removal can be accomplished without deleterious dentin destruction. In effect, the need is for a safer abrasive that exhibits a significantly higher PCR level versus RDA level than has previously been provided within the dental silica industry. Again, the Rice patent is merely a start toward desirable abrasive characteristics. Furthermore, the requirement to produce these separate gel and precipitate materials and meter them out for proper target levels of such characteristics adds costs and process steps to the manufacturing procedure. A manner of providing the benefits of such combinations, but to a very high level of pellicle film cleaning and at a relatively low to moderate degree of dentin abrasion, with simultaneous facilitation of incorporation within dentifrice formulation are thus unavailable to the industry at this time.

The ability to provide low dentin abrasive properties with simultaneously high pellicle film cleaning capabilities, particularly when the ratio of such characteristics is 1 or lower, has heretofore been unattained within the dental industry.

OBJECTS AND SUMMARY OF THE INVENTION

It has now been found that modifications in the processes for producing precipitated silicas can result in the in situ simultaneous production of targeted amounts of silica gels therein, particularly those in which the final structure of the in situ generated composite can be controlled. Such a novel method thus permits the production of in situ generated gel/precipitate silica materials that provide excellent dentin abrasion and pellicle film cleaning capabilities within dentifrices or, in the alternative, such formulations that exhibit excellent thickening properties as well as desirable abrasive and cleaning properties through the introduction of such a singularly produced, stored, and introduced additive. Importantly, as well, is the need to incorporate a high shear treatment step after the initial gel production process has been accomplished. Such an extra procedure provides previously unattained PCR and RDA results, as well as increased brightness of the materials, as described herein.

In particular, the specific in situ formed composites exhibit very high levels pellicle film cleaning properties compared with lower radioactive dentin abrasion results such that the resultant materials can be added with other abrasive materials (such as lower structure precipitated silicas, calcium carbonates, and the like) for the dentifrice producer to target certain high levels of cleaning with lower abrasiveness thus providing the optimization of cleaning while providing a larger margin of abrasion protection to the ultimate user. It is also believed, without intending to be bound to any specific scientific theory, that the increased amount of silica gel within the final composite materials aids in providing narrower particle size ranges in order to contribute a controlled result of high cleaning and reduced dentin abrasion levels. As will be discussed in greater detail below, the physically mixed combination of such materials (i.e., not simultaneously produced within the same reaction) has been found to impart limited levels of such properties, namely the need to provide materials (particularly a precipitated silica component) that exhibits an extremely high, potentially deleterious dentin abrasion level in order to impart, at the same time, an acceptable high pellicle film cleaning level. The novel in situ generated precipitated/gel combination silicas unexpectedly provide a higher degree of pellicle film cleaning with a significantly lower dentin abrasion value, thus according the dentifrice industry not only a potentially more desirable lower abrasive material for better dental protection. It has been realized that the presence of varied amounts of such a silica gel component permits the benefit of the sharp edges exhibited by the gel agglomerates for abrasiveness, with the coexistence of variable levels of silica precipitates of different structures to accord an overall composite exhibiting high cleaning properties. When produced in situ, such a resultant gel/precipitate material provides unexpectedly improved properties as compared with dry blends of such separately produced components, particularly when the production method incorporates high shear flow subsequent to the initial gel production step. Such high shear conditions appear to provide ultimate beneficial results in terms of the composite materials abrasive properties and brightness characteristics. In such a manner, it has been found that although the pellicle film cleaning level is quite high, in fact the resultant dentin abrasion level is limited, thereby imparting an excellent cleaning material without also imparting too high an abrasion level to the target dental substrate.

All parts, percentages and ratios used herein are expressed by weight unless otherwise specified. All documents cited herein are incorporated by reference.

Accordingly, it is one object of the present invention to provide a precipitated silica and gel silica composite material providing improved pellicle film cleaning without an unacceptably high corresponding increase in dentin or enamel abrasion. Another object of the present invention is to provide a new method for the production of such effective precipitated/gel silica combinations wherein such materials are produced simultaneously and in situ, thereby permitting the proper ratios of such materials to be made during production of the materials, rather than during dentifrice production. Also an object of this invention is to provide an in situ generated precipitated/gel silica composite material wherein the brightness of the high PCR, low RDA product silica materials are very high as well.

Accordingly, this invention encompasses a method for producing simultaneously silica gels and precipitated silicas, said method comprising the sequential steps of a) admixing a sufficient amount of an alkali silicate and an acidulating agent together to form a silica gel composition;

b) subsequent to silica gel composition formation, treating the resultant composition under high shear conditions;

c) simultaneously introducing to said silica gel composition of step "b" a sufficient amount of an alkali silicate and an acidulating agent to form a precipitated silica, thereby producing a precipitate/gel silica combination. Encompassed as well within this invention is the product of such a process wherein the silica gel amount present therein is from 5 to 80% by volume of the total precipitated/gel silica resultant simultaneously produced combination. Further encompassed within this invention are the composite materials made therefrom and dentifrice formulations comprising such materials as well as the product of the inventive process noted above.

Generally, synthetic precipitated silicas are prepared by admixing dilute alkali silicate solutions with strong aqueous mineral acids under conditions where aggregation to the sol and gel cannot occur, stirring and then filtering out the precipitated silica. The resulting precipitate is next washed, dried and comminuted to desired size.

Generally, as well, silica gels include silica hydrogels, hydrous gels, aerogels, and xerogels. Silica gels are also formed by reacting alkali silicate solutions with strong acids or vice-versa, to form a hydrosol and aging the newly formed hydrosol to form the hydrogel. The hydrogel is then washed, dried and comminuted to form the desired materials.

As noted above, the separate production of such materials has historically required manufacture of these separate materials, and proper metering of the two together during the incorporation within a dentifrice formulation in such a way as to provide the desired cleaning/abrasion levels thereof.

To the contrary, the inventive method for simultaneous production of such materials permits the producer to target a range of amounts of silica gel and precipitated silica components as well as structures of precipitated components to impart the desired level of cleaning/abrasion through controlled parameters during production, a significant difference from previous physicals mixtures (i.e., dry blends) of such materials through separate incorporation. Basically, the novel method entails targeting the amount of silica gel desired and specifically selecting certain reaction conditions in order to generate such a desired level during amorphous precipitated silica production.

The inventive abrasive compositions are ready-to-use additives in the preparation of oral cleaning compositions, such as dentifrices, toothpastes, and the like, particularly suited as a raw material in a toothpaste making process. Furthermore, such silica products can be utilized in applications wherein sharp edges and lower abrasiveness may be desired, such as, without limitation, foam inhibitors within certain formulations, such as, without limitation, automatic dishwashing detergents. Additional potential uses of such materials include food carriers, rubber additives and carriers, cosmetic additives, personal care additives, plastic anti-blocking additives, and pharmaceutical additives, without limitation.

DETAILED DESCRIPTION OF THE INVENTION

The abrasive and/or thickening combinations used in the present invention are in-situ formed materials that can be readily formulated on demand with other ingredients to prepare oral cleaning compositions having a high cleaning efficacy without causing undue abrasion on tooth surfaces. The essential as well as optional components of the abrasive and/or thickening compositions and related methods of making same of the present invention are described in more detail below.

General Production Method

The silica compositions of the present invention are prepared according to the following two-stage process with a silica gel being formed in the first stage and precipitated silica formed in the second stage. In this process, an aqueous solution of an alkali silicate, such as sodium silicate, is charged into a reactor equipped with mixing means adequate to ensure a homogeneous mixture, and the aqueous solution of an alkali silicate in the reactor preheated to a temperature of between about 40° C. and about 90° C. Preferably, the aqueous alkali silicate solution has an alkali silicate concentration of approximately 3.0 to 35 wt %, preferably from about 3.0 to about 25 wt %, and more preferably from about 3.0 to about 15 wt %. Preferably the alkali silicate is a sodium silicate with a $SiO_2:Na_2O$ ratio of from about 1 to about 4.5, more particularly from about 1.5 to about 3.4. The quantity of alkali silicate charged into the reactor is about 10 wt % to 80 wt % of the total silicate used in the batch. Optionally, an electrolyte, such as sodium sulfate solution, may be added to the reaction medium (silicate solution or water). Next, an aqueous acidulating agent or acid, such as sulfuric acid, hydrochloric acid, nitric acid, phosphoric acid, and so forth (preferably sulfuric acid), added as a dilute solution thereof (e.g., at a concentration of between about 4 to 35 wt %, more typically about 9.0 to 15.0 wt %) is added to the silicate to form a gel. Once the silica gel is produced and the pH adjusted to the desired level, such as between about 3 and 10, the acid addition is stopped and the gel is heated to the batch reaction temperature, preferably between about 65° C. to about 100° C. It is important to note that after this first stage is completed, the produced silica gel is subjected to high shear conditions to modify the gel from its initial produced form. Such high shearing may be performed in any known manner, such as by increased flow rate of liquids added thereto, physical mixing in a blending setting, and the like. The requirement of high shear conditioning is met simply by the modification of the gel component after initial production. Such modification is measurable by a reduction in the average particle size of the gel material after such high shear treatment is undertaken. Preferably, the modification via high shear conditioning is attained once the average particle size of the gel component is reduced at least 5 microns. The resultant gel is otherwise not washed, purified, or cleaned, in any other manner prior to commencement of the second stage.

Next, the second stage begins after the gel reaction temperature is increased, with the simultaneous addition to the reactor of, all while the shear rate remains at the substantially the same level throughout: (1) an aqueous solution of the same acidulating agent previously used and (2) additional amounts of an aqueous solution containing the same species of alkali silicate as is in the reactor, the aqueous solution being preheated to a temperature of about 65° C. to about 100° C. The rate of acidulating agent and silicate additions can be adjusted to control the simultaneous addition pH during the second stage reaction. This pH control can be used to control product physical properties, generally with higher average batch pH providing lower structure silica products and relatively lower average batch pH providing higher structure silica products. In addition to the high shear conditions present already, high shear recirculation may be utilized, and the acid solution addition continues until the reactor batch pH drops to between about 4 to about 9. For purposes of this inventive method, the term "average batch pH" is intended to mean the average pH obtained by measuring the pH level every 5 minutes during the precipitate formation stage and averaging the total aggregate over total time elapsed.

After the inflows of the acidulating agent and the alkali silicate are stopped, the reactor batch allowed to age or "digest" for between 5 minutes to 30 minutes, with the reactor contents being maintained at a constant pH. After the completion of digestion, the high shear mixing, etc., is curtailed, and the resultant reaction batch is filtered and washed with water to remove excess by-product inorganic salts until the wash water from the silica filter cake results in at most 5% salt byproduct content as measured by conductivity.

The silica filter cake is slurried in water, and then dried by any conventional drying techniques, such as spray drying, to produce an amorphous silica containing from about 3 wt % to about 50 wt % of moisture. The silica may then be milled to obtain the desired median particle size of between about 3 μm to 25 μm, preferably between about 3 μm to about 20 μm. Classification of even narrower median particle size ranges may aid in providing increased cleaning benefits as well.

In addition to the above-described production process methodologies of precipitating the synthetic amorphous silicas, the preparation of the silica products is not necessarily limited thereto and it also can be generally accomplished in accordance with the methodologies described, for example, in prior U.S. Pat. Nos. 3,893,840, 3,988,162, 4,067,746, 4,340,583, and 5,891,421, all of which are incorporated herein by reference, as long as such methods are appropriately modified to incorporate recirculation and high shear treatments. As will be appreciated by one skilled in the art, reaction parameters which affect the characteristics of the resultant precipitated silica include: the rate and timing at which the various reactants are added; the levels of concentration of the various reactants; the reaction pH; the reaction temperature; the agitation of the reactants during production; and/or the rate at which any electrolytes are added.

Alternative methods of production for this inventive material include in slurry form such as, without limitation, procedures taught within U.S. Pat. No. 6,419,174, to McGill et al., as well as filter press slurry processes as described within and throughout U.S. Published Pat. Appl. No. 20030019162 to Huang.

The inventive in situ generated composites (also referred to as "combinations") of silica gel and precipitate are useful as high-cleaning, dental abrasives with correlative lower abrasiveness (with low RDA measurements of at most about 110, for instance, and as low as about 70). The in situ process of this invention has thus surprisingly yielded, with degrees of selectivity followed in terms of reaction pH, reactant concentrations, amount of gel component, high shear production conditions, and, as a result, overall structure of the resultant gel/precipitate silica composite materials made therefrom, a method for producing a mid-range product (relatively high, cleaning levels with lower abrasion levels) composites as. Thus, selection of differing concentrations, pH levels, ultimate gel proportions, among other things, can produce gel/precipitate silica composite materials of overall medium structures in order to accord relatively high pellicle film cleaning results, with lower abrasive properties as compared with the high cleaning materials described above.

For this cleaning material, the gel component is present in an amount between 10 and 60% by weight of the ultimately formed gel/precipitate silica composite material (and thus the precipitated silica component is present in an amount of from 90 to 40% by weight as a result). The overall amount of gel to be produced is preferably relatively low (from up to 40%, for instance). Such percentages of gel component actually represent the volume amount of silicate present during the production phases for each different silica material, as described above for the high cleaning material.

Generally, it has been determined that such specific mid-range cleaning abrasives may be produced through a method of admixing a suitable acid and a suitable silicate starting material (wherein the acid concentration, in aqueous solution, is from 5 to 25%, preferably from 10 to 20%, and more preferably from 10 to 12%, and the concentration of the silicate starting material is from 4 to 35%, also within an aqueous solution), to initially form a silica gel. Subsequent to gel formation, sufficient silicate and acid are added (without any washing, or other type of purification, or physical modification of the gel) to the formed gel for further production of appropriately structured precipitated silica component desired for a mid-range cleaning composite material to be formed. The pH of the overall reaction may be controlled anywhere within the range of 3 to 10. Depending on the amount of gel initially formed, the amount and structure of precipitated silica component may be targeted in much the same way as for the high cleaning material. It has been realized that in order to provide a mid-range cleaning, low abrasive material through this process, the amount of gel is preferably higher (as noted above, from 10 to 60% by volume of the composite, preferably from 20 to 33%) and the amount of low structure precipitated silica is preferably lower (from 90 to 40% by volume of the composite, preferably from 80 to 67%).

Broadly, the inventive mid-range cleaning gel/precipitated silica combination generally have the following properties: 10% Brass Einlehner hardness values in the range between 2.5 and 12.0, and, within a test dentifrice formulation (as presented below within the examples) RDA (Radioactive Dentin Abrasion) values between about 80 to about 120, and (within the same test dentifrice formulation) PCR (Pellicle Cleaning Ratio) values of 80 to 120, with a ratio of PCR to RDA within the range of 0.7 to 1.0.

Dentifrice Uses of the Inventive Materials

The inventive in situ generated gel/precipitate silica composite materials described herein may be utilized alone as the cleaning agent component provided in the dentifrice compositions of this invention, or as an additive with other abrasive materials therein. A combination of the inventive composite materials with other abrasives physically blended therewith in a suitable dentifrice formulation is potentially preferred in this regard in order to accord targeted dental cleaning and abrasion results at a desired protective level. Thus, any number of other conventional types of abrasive additives may be present within inventive dentifrices in accordance with this invention. Other such abrasive particles include, for example, and without limitation, precipitated calcium carbonate (PCC), ground calcium carbonate (GCC), dicalcium phosphate or its dihydrate forms, silica gel (by itself, and of any structure), amorphous precipitated silica (by itself, and of any structure as well), perlite, titanium dioxide, calcium pyrophosphate, hydrated alumina, calcined alumina, insoluble sodium metaphosphate, insoluble potassium metaphosphate, insoluble magnesium carbonate, zirconium silicate, aluminum silicate, and so forth, can be introduced within the desired abrasive compositions to tailor the polishing characteristics of the target formulation (dentifrices, for example, etc.), if desired, as well.

The precipitate/gel silica combination described above, when incorporated into dentifrice compositions, is present at a level of from about 5% to about 50% by weight, more preferably from about 10% to about 35% by weight, particularly when the dentifrice is a toothpaste. Overall dentifrice or oral cleaning formulations incorporating the abrasive compositions of this invention conveniently can comprise the following possible ingredients and relative amounts thereof (all amounts in wt %):

Dentifrice Formulation

| Ingredient | Amount |
| --- | --- |
| Liquid Vehicle: | |
| humectant(s) (total) | 5-70 |
| deionized water | 5-70 |
| binder(s) | 0.5-2.0 |
| anticaries agent | 0.1-2.0 |
| chelating agent(s) | 0.4-10 |
| silica thickener* | 3-15 |
| surfactant(s) | 0.5-2.5 |
| abrasive | 10-50 |
| sweetening agent | <1.0 |
| coloring agents | <1.0 |
| flavoring agent | <5.0 |
| preservative | <0.5 |

In addition, as noted above, the inventive abrasive could be used in conjunction with other abrasive materials, such as precipitated silica, silica gel, dicalcium phosphate, dicalcium phosphate dihydrate, calcium metasilicate, calcium pyrophosphate, alumina, calcined alumina, aluminum silicate, precipitated and ground calcium carbonate, chalk, bentonite, particulate thermosetting resins and other suitable abrasive materials known to a person of ordinary skill in the art.

In addition to the abrasive component, the dentifrice may also contain one or more organoleptic enhancing agents. Organoleptic enhancing agents include humectants, sweeteners, surfactants, flavorants, colorants and thickening agents, (also sometimes known as binders, gums, or stabilizing agents), Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, as well as mixtures of these compounds. Typical levels of humectants are from about 20 wt % to about 30 wt % of a toothpaste composition.

Sweeteners may be added to the toothpaste composition to impart a pleasing taste to the product. Suitable sweeteners include saccharin (as sodium, potassium or calcium saccharin), cyclamate (as a sodium, potassium or calcium salt), acesulfame-K, thaumatin, neohisperidin dihydrochalcone, ammoniated glycyrrhizin, dextrose, levulose, sucrose, mannose, and glucose.

Surfactants are used in the compositions of the present invention to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine and the like. Sodium lauryl sulfate is a preferred surfactant. The surfactant is typically present in the oral care compositions of the present invention in an amount of about 0.1 to about 15% by weight, preferably about 0.3% to about 5% by weight, such as from about 0.3% to about 2%, by weight.

Flavoring agents optionally can be added to dentifrice compositions. Suitable flavoring agents include, but are not limited to, oil of wintergreen, oil of peppermint, oil of spearmint, oil of sassafras, and oil of clove, cinnamon, anethole, menthol, thymol, eugenol, eucalyptol, lemon, orange and other such flavor compounds to add fruit notes, spice notes, etc. These flavoring agents consist chemically of mixtures of aldehydes, ketones, esters, phenols, acids, and aliphatic, aromatic and other alcohols.

Colorants may be added to improve the aesthetic appearance of the product. Suitable colorants are selected from colorants approved by appropriate regulatory bodies such as the FDA and those listed in the European Food and Pharmaceutical Directives and include pigments, such as $TiO_2$, and colors such as FD&C and D&C dyes.

Thickening agents are useful in the dentifrice compositions of the present invention to provide a gelatinous structure that stabilizes the toothpaste against phase separation. Suitable thickening agents include silica thickener; starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; as well as mixtures of these compounds. Typical levels of thickening agents or binders are from about 0 wt % to about 15 wt % of a toothpaste composition.

Therapeutic agents are optionally used in the compositions of the present invention to provide for the prevention and treatment of dental caries, periodontal disease and temperature sensitivity. Examples of therapeutic agents, without intending to be limiting, are fluoride sources, such as sodium fluoride, sodium monofluorophosphate, potassium monofluorophosphate, stannous fluoride, potassium fluoride, sodium fluorosilicate, ammonium fluorosilicate and the like; condensed phosphates such as tetrasodium pyrophosphate, tetrapotassium pyrophosphate, disodium dihydrogen pyrophosphate, trisodium monohydrogen pyrophosphate; tripolyphosphates, hexametaphosphates, trimetaphosphates and pyrophosphates, such as; antimicrobial agents such as triclosan, bisguanides, such as alexidine, chlorhexidine and chlorhexidine gluconate; enzymes such as papain, bromelain, glucoamylase, amylase, dextranase, mutanase, lipases, pectinase, tannase, and proteases; quarternary ammonium compounds, such as benzalkonium chloride (BZK), benzethonium chloride (BZT), cetylpyridinium chloride (CPC), and domiphen bromide; metal salts, such as zinc citrate, zinc chloride, and stannous fluoride; sanguinaria extract and sanguinarine; volatile oils, such as eucalyptol, menthol, thymol, and methyl salicylate; amine fluorides; peroxides and the like. Therapeutic agents may be used in dentifrice formulations singly or in combination at a therapeutically safe and effective level.

Preservatives may also be optionally added to the compositions of the present invention to prevent bacterial growth. Suitable preservatives approved for use in oral compositions such as methylparaben, propylparaben and sodium benzoate may be added in safe and effective amounts.

The dentifrices disclosed herein may also a variety of additional ingredients such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like Water provides the balance of the composition in addition to the additives mentioned. The water is preferably deionized and free of impurities. The dentifrice will usually comprise from about 20 wt % to about 35 wt % of water.

Useful silica thickeners for utilization within such a toothpaste formulation include, as a non-limiting example, an amorphous precipitated silica such as ZEODENT® 165 silica. Other preferred (though non-limiting) silica thickeners are ZEODENT® 163 and/or 167 and ZEOFREE®153, 177, and/or 265 silicas, all available from J. M. Huber Corporation, Havre de Grace Md., U.S.A.

For purposes of this invention, a "dentifrice" has the meaning defined in Oral Hygiene Products and Practice, Morton Pader, Consumer Science and Technology Series, Vol. 6, Marcel Dekker, NY 1988, p. 200, which is incorporated herein by reference. Namely, a "dentifrice" is " . . . a substance used with a toothbrush to clean the accessible surfaces of the teeth. Dentifrices are primarily composed of water, detergent, humectant, binder, flavoring agents, and a finely powdered abrasive as the principal ingredient . . . a dentifrice is considered to be an abrasive-containing dosage form for delivering anti-caries agents to the teeth." Dentifrice formulations contain ingredients which must be dissolved prior to incorporation into the dentifrice formulation (e.g. anti-caries agents such as sodium fluoride, sodium phosphates, flavoring agents such as saccharin).

The various silica and toothpaste (dentifrice) properties described herein were measured as follows, unless indicated otherwise.

The Brass Einlehner (BE) Abrasion test used to measure the hardness of the precipitated silicas/silica gels reported in this application is described in detail in U.S. Pat. No. 6,616,916, incorporated herein by reference, involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams brass lost from the Fourdrinier wire screen per 100,000 revolutions. The result, measured in units of mg loss, can be characterized as the 10% brass Einlehner (BE) abrasion value.

The oil absorption values are measured using the rubout method. This method is based on a principle of mixing linseed oil with a silica by rubbing with a spatula on a smooth surface until a stiff putty-like paste is formed. By measuring the quantity of oil required to have a paste mixture which will curl when spread out, one can calculate the oil absorption value of the silica—the value which represents the volume of oil required per unit weight of silica to saturate the silica sorptive capacity. A higher oil absorption level indicates a higher structure of precipitated silica; similarly, a low value is indicative of what is considered a low-structure precipitated silica. Calculation of the oil absorption value was done as follows:

$$\text{Oil absorbtion} = \frac{\text{ml oil absorbed}}{\text{weight of silica, grams}} \times 100$$

$$= \text{ml oil}/100 \text{ gram silica}$$

Median particle size is determined using a Model LA-930 (or LA-300 or an equivalent) laser light scattering instrument available from Horiba Instruments, Boothwyn, Pa.

The % 325 mesh residue of the inventive silica is measured utilizing a U.S. Standard Sieve No. 325, with 44 micron or 0.0017 inch openings (stainless steel wire cloth) by weighing a 10.0 gram sample to the nearest 0.1 gram into the cup of the 1 quart Hamilton mixer Model No. 30, adding approximately 170 ml of distilled or deionized water and stirring the slurry for at least 7 min. Transfer the mixture onto the 325 mesh screen; wash out the cup and add washings onto the screen. Adjust water spray to 20 psi and spray directly on screen for two minutes. (Spray head should be held about four to six inches above the screen cloth. Wash the residue to one side of the screen and transfer by washing into an evaporating dish using distilled or deionized water from a washing bottle. Let stand for two to three minutes and decant the clear water. Dry (convection oven@150° C. or under infrared oven for approx. 15 min.) cool and weigh residue on analytical balance.

Moisture or Loss on Drying (LOD) is the measured silica sample weight loss at 105° C. for 2 hours. Loss on ignition (LOI) is the measured silica sample weight loss at 900° C. for 2 hours (sample previously predried for 2 hours at 105° C.).

The pH values of the reaction mixtures (5 weight % slurry) encountered in the present invention can be monitored by any conventional pH sensitive electrode.

To measure brightness, fine powder materials pressed into a smooth surfaced pellet were evaluated using a Technidyne Brightmeter S-5/BC. This instrument has a dual beam optical system where the sample is illuminated at an angle of 45°, and the reflected light viewed at 00. It conforms to TAPPI test methods T452 and T646, and ASTM Standard D985. Powdered materials are pressed to about a 1 cm pellet with enough pressure to give a pellet surface that is smooth and without loose particles or gloss.

The Radioactive Dentin Abrasion (RDA) values of dentifrices containing the silica compositions used in this invention are determined according to the method set forth by Hefferen, Journal of Dental Res., July-August 1976, 55 (4), pp. 563-573, and described in Wason U.S. Pat. Nos. 4,340,583, 4,420,312 and 4,421,527, which publications and patents are incorporated herein by reference.

The cleaning property of dentifrice compositions is typically expressed in terms of Pellicle Cleaning Ratio ("PCR") value. The PCR test measures the ability of a dentifrice composition to remove pellicle film from a tooth under fixed brushing conditions. The PCR test is described in "In Vitro Removal of Stain With Dentifrice" G. K. Stookey, et al., J. Dental Res., 61, 1236-9, 1982. Both PCR and RDA results vary depending upon the nature and concentration of the components of the dentifrice composition. PCR and RDA values are unitless.

PREFERRED EMBODIMENTS OF THE INVENTION

The inventive materials were prepared by sequentially forming (in situ) a first silica gel (or gel-like material) and adding thereto sufficient amounts of reactants to form a precipitated silica component present simultaneously with the initially produced gel (or gel-like material). The amount of gel is controlled by the quantity of reactants in the first stage while the amount of precipitated silica is controlled by the quantity of reactants in the second stage. The structure of the final product is controlled by the amount of gel first produced as related to the amount of precipitated silica, as well as reaction parameters, such as temperature, rates, concentrations, pH, and so forth, as discussed in greater detail above.

EXAMPLE

The inventive example initially involved the provision of 8140 liters of 6.0% sodium silicate to which was added 11.4% sulfuric acid at a rate of 191.3 liters/minute for 8 minutes at a temperature of 50° C. within a reactor. The resultant silica gel-containing slurry was then heated up to 93° C. for 53 minutes thereafter. Subsequently, 13 minutes into the heating step, high shear flow of 3000 liters/minute of reactor slurry (gel) was started and continued throughout the remainder of the example production. After the 53 minutes completed, 30 kilograms of dry weight of sulfuric acid (243.8 liters) was then added to the gel slurry. Thereafter, simultaneous sulfuric acid and sodium silicate addition was started with introduction of both to the reactor to initiate the precipitation step. The sodium silicate of 16.21% concentration (at a temperature of 85° C.) was added at 339 liters/minute and dilute sulfuric acid (11.4% concentration) was introduced at 191.3 liters/minute. The silicate was added for a duration of 48 minutes. The acid was added until the pH of the resultant slurry was dropped to 7.0. At that point, the acid flow was reduced to 110 liters/minute until the pH was between 5.3 and 5.5, at which point acid addition was stopped. The resultant composition was then allowed to digest for another 10 minutes at 93° C. The resultant slurry was then recovered by filtration, washed to a sodium sulfate concentration of less than about 5% (preferably less than 4%, and most preferably below 2%) as determined by monitoring the filtrate conductivity and then spray dried to a level of about 5% moisture. The dried product was then milled to uniform size.

COMPARATIVE EXAMPLE

The same basic method as above was followed, except that no high shear conditions after gel formation were utilized.

Certain properties of the resultant materials from the Example and Comparative Example were then measured. The following table shows those results:

TABLE 1

| Material Properties | | |
|---|---|---|
| Example | Ex. | Comp. |
| % moisture | 3.4 | 4.1 |
| % LOI | 2.9 | 2.8 |
| % 325 Mesh Residue | 0 | 0 |
| 5% pH | 7.0 | 7.21 |
| Brightness (technidyne) | 96 | 94.6 |
| Average Particle Size, μm | | |
| Median Particle Size (Horiba) | 9.64 | 9.35 |
| Mean Particle Size (Horiba) | 10.95 | 10.64 |
| Einlehner Abrasion (mg loss/100,000 rev) | 3.53 | 6.17 |
| Oil Absorption (cc/100 g) | 105 | 99 |

A brightness of at least 95.5 is a significant improvement over the comparative type and is thus the low end of the brightness level of the inventive materials.

Dentifrice Formulations

Toothpaste formulations were prepared using the above-described gel/precipitated silica example and comparative example to demonstrate the ready-to-use on demand capabilities of the inventive compositions without furthering metering of the two components for optimum dental protection benefits.

To prepare the dentifrices, the glycerin, sodium carboxymethyl cellulose, polyethylene glycol and sorbitol were mixed together and stirred until the ingredients were dissolved to form a first admixture. The deionized water, sodium fluoride, tetrasodium pyrophosphate and sodium saccharin were also mixed together and stirred until these ingredients are dissolved to form a second admixture. These two admixtures were then combined with stirring. Thereafter, the optional color was added with stirring to obtain a "pre-mix". The pre-mix was placed in a Ross mixer (Model 130 LDM) and silica thickener, abrasive silica and titanium dioxide were mixed in without vacuum. A 30-inch vacuum was drawn and the resultant admixture was stirred for approximately 15 minutes. Lastly, sodium lauryl sulfate and flavor were added and the admixture was stirred for approximately 5 minutes at a reduced mixing speed. The resultant dentifrice was transferred to plastic laminate toothpaste tubes and stored for future testing. The dentifrice formulations are given in Table 2 below. The dentifrice formulation utilized was considered a suitable test dentifrice formulation for the purposes of determining PCR and RDA measurements for the inventive and comparative cleaning abrasives.

TABLE 2

|  | Example Formulation | Comparative Formulation |
| --- | --- | --- |
| Glycerin (99.5%), % | 11 | 11 |
| Sorbitol (70%), % | 40 | 40 |
| Deionized water, % | 20 | 20 |
| CARBOWAX ® 600[1], % | 3 | 3 |
| CEKOL ® 500T CMC[2], % | 1.2 | 1.2 |
| Tetrasodium pyrophosphate | 0.5 | 0.5 |
| Sodium Saccharin, % | 0.2 | 0.2 |
| Sodium Fluoride, % | 0.243 | 0.243 |
| Silica thickener Zeodent ® 165[3], | 1.5 | 1.5 |
| Example abrasive, % | 20 |  |
| Comp. Example abrasive, % |  | 20 |
| $TiO_2$, % | 0.5 | 0.5 |
| Sodium lauryl sulfate, % | 1.2 | 1.2 |
| Flavor, % | 0.65 | 0.65 |

[1] A polyethylene glycol available from Dow Chemical Company, Midland, MI
[2] A carboxymethylcellulose available from CPKelco Oy, Arnhem, The Netherlands
[3] An amorphous, precipitated high structure silica thickening available from J.M. Huber Corporation, Havre de Grace, MD The dentifrice formulations prepared above were evaluated for PCR and RDA properties, according to the methods described above; the measurements, as well as the PCR:RDA ratios for each dentifrice formulation are provided in Table 3 below.

TABLE 3

|  | Example Formulation | Comparative Formulation |
| --- | --- | --- |
| PCR | 85 | 87 |
| RDA | 88 | 113 |
| PCR/RDA | 0.97 | 0.77 |

The results show highly effective cleaning capabilities with relatively low dentin abrasion properties for both examples, but much pronounced improvement in the inventive example in terms of lowered RDA with very low ratio of PCR/RDA. A ratio of as close to 1.0 is preferred; thus, above 0.8 is desired, with above 0.85 more preferred, above 0.90 still more preferred, and above 0.95 most preferred.

While the invention will be described and disclosed in connection with certain preferred embodiments and practices, it is in no way intended to limit the invention to those specific embodiments, rather it is intended to cover equivalent structures structural equivalents and all alternative embodiments and modifications as may be defined by the scope of the appended claims and equivalence thereto.

The invention claimed is:

1. An in situ produced gel/precipitate silica composite, wherein said composite exhibits a technidyne brightness of at least 95.5, and, when incorporated into a dentifrice composition in an amount of 20% by weight, said dentifrice exhibits a RDA (Radioactive Dentin Abrasion) of at most 120, and a PCR (Pellicle Cleaning Ratio):RDA ratio of from 0.7 to 1.0.

2. A dentifrice comprising the gel/precipitate composite of claim 1.

3. The gel/precipitate silica composite of claim 1 wherein said dentifrice exhibits a PCR:RDA ratio of from 0.8 to 1.0.

4. A dentifrice comprising the gel/precipitate composite of claim 3.

5. The gel/precipitate silica composite of claim 3 wherein said dentifrice exhibits a PCR:RDA ratio of from 0.85 to 1.0.

6. A dentifrice comprising the gel/precipitate composite of claim 5.

7. The gel/precipitate silica composite of claim 5 wherein said dentifrice exhibits a PCR:RDA ratio of from 0.9 to 1.0.

8. A dentifrice comprising the gel/precipitate composite of claim 7.

9. The gel/precipitate silica combination of claim 7 wherein said dentifrice exhibits a PCR:RDA ratio of from 0.95 to 1.0.

10. A dentifrice comprising the gel/precipitate composite of claim 9.

* * * * *